United States Patent [19]

Liu

[11] Patent Number: 4,720,578

[45] Date of Patent: Jan. 19, 1988

[54] PREPARATION OF FLUORINATED CARBOXYPROPYLATED NON-IONIC SURFACTANTS

[75] Inventor: Kou-Chang Liu, Wayne, N.J.

[73] Assignee: GAF Corporation, Wayne, N.J.

[21] Appl. No.: 887,299

[22] Filed: Jul. 23, 1986

[51] Int. Cl.$^4$ .............................. C07C 143/74
[52] U.S. Cl. ..................... 562/556; 562/586
[58] Field of Search ................ 562/556, 567, 586

[56] References Cited

U.S. PATENT DOCUMENTS

| | | | |
|---|---|---|---|
| 2,352,641 | 7/1944 | Kung | 562/588 |
| 2,449,991 | 9/1946 | Gresham | 562/471 |
| 4,160,777 | 7/1979 | Loudas | 562/556 |
| 4,239,915 | 12/1980 | Falk | 562/556 |

FOREIGN PATENT DOCUMENTS

| | | | |
|---|---|---|---|
| 60-106566 | 6/1985 | Japan | 562/556 |
| 60-173096 | 9/1985 | Japan | 562/556 |
| 61-143750 | 7/1986 | Japan | 562/556 |

*Primary Examiner*—Michael L. Shippen
*Attorney, Agent, or Firm*—Marilyn J. Maue; Joshua J. Ward

[57] ABSTRACT

The invention relates to a non-ionic surfactant having the formula:

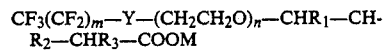

and to the process for the preparation and use of said surfactants. The process involves reacting an alcohol ether, $CF_3(CF_2)_m-Y-(CH_2CH_2O)_nH$, with a metal hydroxide, MOH, to produce the corresponding intermediate salt,

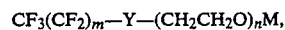

and reacting said salt with a butyrolactone,

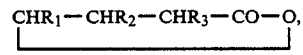

to produce the corresponding carboxypropylated product shown above, wherein Y is oxygen or $-SO_2N'-R$ where R is lower alkyl; $R_1$, $R_2$ and $R_3$ are each independently hydrogen or $C_1$ to $C_4$ alkyl; M is a sodium, potassium or lithium cation; n is an integer having a value of from 2 to 50 and m is an integer having a value of from 3 to 25.

14 Claims, No Drawings

PREPARATION OF FLUORINATED CARBOXYPROPYLATED NON-IONIC SURFACTANTS

BACKGROUND OF THE INVENTION

Prior processes have prepared carboxy alkylated surfactants by reacting 1 mole of a high molecular weight alcohol ether with 2 moles of inorganic hydroxide in flake form followed by the addition of chloroacetic acid, a known skin irritant, to produce the corresponding non-ionic surfactant. However, this process generates eye and skin irritating alkali metal chloride by-product which is difficult and expensive to separate from the desired product. Also, the process requies a 1 mole excess of hydroxide reactant which is consumed in the reaction to form waste by-product metal chloride. Accordingly, the process makes inefficient use of the hydroxide to achieve alkylated surfactant product and involves time consuming, purification steps which must be employed where the product is to be used as a surfactant in cosmetic or medicinal applications.

Accordingly, it is an object of the present process to eliminate these deficiencies while providing an economical and commercially feasible process for making an impproved surfactant.

Another object is to provide a process for the preparation of a new carboxypropylated surfactant having superior wetting and leveling properties in a high state of purity and in yields above 85%.

Still another object is to provide a process which eliminates the use of a haloacetic acid irritant and which produces a non-ionic carboxypropylated surfactant.

Yet another object is to provide a process in which the chain length of the surfactant molecule can be extended and regulated by proper selection of adduct coreactant.

These and other objects will become apparent from the following description and disclosure.

THE INVENTION

According to this invention there is provided a novel fluorinated surfactant having the formula:

$$CF_3(CF_2)_m-Y-(CH_2CH_2O)_n-CHR_1-CHR_2-CHR_3-COOM \quad \text{A.}$$

in a high state of purity, wherein m has a value of from 3 to 25, preferably from 4 to 20; n has an average value of from 2 to 50, preferably 3 to 20; Y is oxygen or $-SO_2N'-R$, where R is lower alkyl; $R_1$, $R_2$ and $R_3$ are each independently selected from the group of hydrogen and alkyl having from 1 to 4 carbon atoms and M is a cation such as $Na^+$, $K^+$ or $Li^+$.

The fluorinated surfactants of the present invention exhibit superior wetting and leveling properties and possess high flash points which render them substantially non-flammable. They are beneficially employed in dry cleaning formulations, in floor polish and automobile polish formulations, etc., in concentrations between about 0.01 and about 2 weight %. The fluorinated surfactants herein described are also employed in high solids or solvent-free coatings, e.g., in high solids epoxy coatings, to impart wetting and leveling. For this purpose, the amount of fluorinated surfactant may be somewhat higher than that employed in polish formulations.

The present surfactants are produced by the process which involves the reaction of a metal hydroxide, such as sodium, potassium or lithium hydroxide, with an alcohol ether having the formula:

$$CF_3(CF_2)_m-Y-(CH_2CH_2O)_nH \quad \text{B.}$$

to produce the corresponding intermediate salt having the formula:

$$CF_3(CF_2)_m-Y-(CH_2CH_2O)_nM \quad \text{C.}$$

The water generated during the hydroxide condensation reaction can be removed, e.g. by venting to the atmosphere or the water of reaction can be allowed to remain in the system and be recovered with the final product, as a carrier therefor, suitable for direct incorporation into detergent and cosmetic formulations. The intermediate salt formed by the condensation reaction is then reacted with a butyrolactone having the formula:

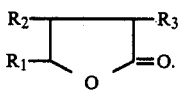

In the above formulae B, C and D, the components m, n, M, Y, $R_1$, $R_2$ and $R_3$ have the same definitions as set forth above in Formula A.

The above reaction can be summarized by the equation:

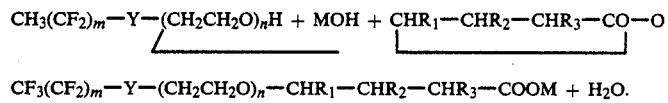

$$CF_3(CF_2)_m-Y-(CH_2CH_2O)_n-CHR_1-CHR_2-CHR_3-COOM + H_2O.$$

The above reactions can be carried out in the presence or absence of an inert solvent such as for example, N-methyl pyrrolidone, chlorobenzene, toluene, xylene, cyclohexane, tetrahydrofuran, or an excess of the butyrolactone reactant. The concentration of solvent, when used, is not critical. For example 20–40% by weight of the active components in the reaction may be used. While the alcohol ether, inorganic hydroxide and butyrolactone can be intermixed and reacted in a one stage operation, the synthesis can also be carried out in two stages, namely by reacting the alcohol ether with the inorganic hydroxide in a first stage and then reacting the resulting ether salt with the butyrolactone in a second stage of the process to produce the surfactant of the present invention. For economic considerations, the mole ratio of alcohol ether to hydroxide fed to the reaction zone should be close to stoichiometry.

It will become apparent that the molecular weight of the surfactant molecule can be regulated by selection of the alcohol ether and/or butyrolactone reactants, which coreactant can have as many as 16, and as few as 4, carbon atoms in the molecule.

In general the above reactions are carried out at temperatures between about 25° and about 235° C. under atmospheric pressure for a period of from about 0.1 to about 50 hours; although it should be pointed out that higher reaction temperatures, for example up to 300° C.

under superatmospheric pressure e.g. about 70 psig, can be employed when desired. For optimum results, it is recommended that the reaction be carried out with agitation and preferably at a temperature between about 50° and about 200° C. under atmospheric pressure for a period of from about 1 to about 20 hours.

Since the components of the present reaction are non-corrosive, acid resistant equipment is not required and since only a stoichiometric proportion of the alcohol ether and inorganic hydroxide need be employed the product can be obtained in yields greater than about 90%.

Among the alcohol ethers illustrating the primary reactant of the present invention, there is mentioned the fluorinated straight chain and branched chain species of butyl, amyl, hexyl, heptyl, octyl, nonyl, decyl, dodecyl, tetradecyl, octadecyl, etc. and intermixtures of alcohol ethers within the scope of this invention as herein described.

Representative of the butyrolactones included within the scope of this invention are butyrolactone, methyl butyrolactone, dimethyl butyrolactone, ethyl butyrolactone, tributyl butyrolactone, diethyl butyrolactone and triethyl butyrolactone.

Having thus described the invention, reference is now had to the following examples which are not to be construed as limiting to the scope of the invention described herein and as set forth in the appended claims. All ratios and amounts reported in the following examples are by weight unless otherwise indicated.

EXAMPLE I

Into a 250 ml three necked, round bottom flask, equipped with a thermometer, a mechanical stirrer and a vacuum line, was introduced 118.6 g of FLUORAD FC-170,

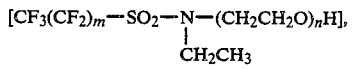

and 10.2 g. of potassium hydroxide. The mixture was heated to 110° C. under reduced pressure of 10 mm Hg for 3 hours. After the removal of water, 30.3 g. of γ-butyrolactone was added and the solution heated at 112° C. for an additional 3 hours. The corresponding carboxypropylated perfluoroalkyl ethylene oxide potassium salt product, having the formula: $CF_3(CF_2)_m$—$SO_2N$—$(CH_2CH_2O)_nK$, was recovered in about 80% yield.

What is claimed is:

1. The process which comprises reacting an alcohol ether having the formula:

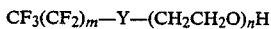

with a metal hydroxide having the formula MOH to produce the corresponding salt having the formula:

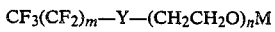

and reacting said salt with a butyrolactone having the formula:

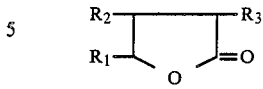

to produce the corresponding carboxypropylated polyethylene glycol salt product having the formula

wherein Y is oxygen or —$SO_2N$—R where R is alkyl having from 1 to 4 carbon atoms; $R_1$, $R_2$ and $R_3$ are each independently hydrogen or alkyl having from 1 to 4 carbon atoms; M is a sodium, potassium or lithium cation; n is an integer having a value of from 2 to 50 and m is an integer having a value of from 3 to 25.

2. The process of claim 1 in which the reaction is carried out at a temperature between about 25° C. and about 300° C. under a pressure of from about 12 psig. to about 70 psig. for a period of from about 1 to about 20 hours.

3. The process of claim 1 wherein the process is carried out in two stages and wherein the reaction of the alcohol ether and a metal hydroxide to produce a salt represents the first stage and the reaction of said salt and said butyrolactone represents the second stage and wherein both reactions are carried out at a temperature of between about 25° C. and about 235° C.

4. The process of claim 1 wherein the process is carried out in a single stage and the alcohol ether, metal hydroxide and butyrolactone are intermixed in the reaction zone.

5. The process of claim 1 wherein the mole ratio of alcohol ether to metal hydroxide is about 1:1.

6. The process of claim 1 wherein water is generated in the reaction between the alcohol ether and the metal hydroxide and the water of reaction is recovered with the product.

7. The process of claim 1 wherein water is generated in the reaction between the alcohol ether and the metal hydroxide and the water of reaction is removed prior to the addition of the butyrolactone.

8. The process of claim 1 wherein the reaction is carried out in the presence of an inert solvent.

9. The process of claim 8 wherein said solvent is selected from the group consisting of toluene, xylene, cyclohexane, butyrolactone, N-methyl pyrrolidone, chlorobenzene, tetrahydrofuran and mixtures thereof.

10. The process of claim 9 wherein the solvent is n-butyrolactone.

11. The process of claim 1 wherein the hydroxide is sodium hydroxide.

12. The process of claim 1 wherein the hydroxide is potassium hydroxide.

13. The process of claim 1 wherein said alcohol ether is perfluorooctyl alcohol having an average of 7 ethylene oxide units.

14. The process of claim 1 wherein said alcohol ether is perfluorohexyl alcohol having an average of 8 ethylene oxide units.

* * * * *